United States Patent
De La Mettrie

(10) Patent No.: US 7,481,845 B2
(45) Date of Patent: *Jan. 27, 2009

(54) COMPOSITION FOR PROTECTING KERATIN MATERIAL, PROCESS OF MAKING, USES THEREOF

(75) Inventor: Roland De La Mettrie, Le Vesinet (FR)

(73) Assignee: L'Oreal, Paris (FR)

( * ) Notice: Subject to any disclaimer, the term of this patent is extended or adjusted under 35 U.S.C. 154(b) by 219 days.

This patent is subject to a terminal disclaimer.

(21) Appl. No.: 11/040,001

(22) Filed: Jan. 24, 2005

(65) Prior Publication Data

US 2005/0166336 A1     Aug. 4, 2005

Related U.S. Application Data

(60) Provisional application No. 60/545,188, filed on Feb. 18, 2004.

(30) Foreign Application Priority Data

Jan. 29, 2004   (FR)   ................... 04 00851

(51) Int. Cl.
*A61Q 5/10*   (2006.01)
*A61K 8/02*   (2006.01)

(52) U.S. Cl. ................ 8/405; 8/431; 8/469; 8/472; 8/505; 132/202; 132/208; 424/401

(58) Field of Classification Search ............ 8/405, 8/431, 469, 472, 505, 408, 472.505; 132/202, 132/208; 424/401
See application file for complete search history.

(56) References Cited

U.S. PATENT DOCUMENTS 2,526,607 A   10/1950   Kurth
5,895,672 A   4/1999   Cooper
6,146,616 A   11/2000   Msika et al.
6,468,564 B1   10/2002   Riley et al.
7,018,428 B2 *   3/2006   Grollier et al. ............... 8/405
2002/0009533 A1   1/2002   Forturne, Jr.
2003/0096038 A1   5/2003   Cai

FOREIGN PATENT DOCUMENTS

EP    0 384 796    8/1990
FR    2 207 699    11/1972

OTHER PUBLICATIONS

U.S. Appl. No. 11/039,781, filed Jan. 24, 2005, Grollier.
U.S. Appl. No. 11/040,001, filed Jan. 24, 2005, De La Mettrie.
U.S. Appl. No. 11/030,193, filed Jan. 7, 2005, De La Mettrie.
U.S. Appl. No. 11/033,118, filed Jan. 12, 2005, De La Mettrie.
U.S. Appl. No. 11/033,119, filed Jan. 12, 2005, De La Mettrie.
U.S. Appl. No. 11/041,855, filed Jan. 25, 2005, De La Mettrie, et al.
U.S. Appl. No. 11/037,376, filed Jan. 19, 2005, De La Mettrie.
U.S. Appl. No. 11/045,265, filed Jan. 31, 2005, De La Mettrie.
U.S. Appl. No. 11/039,874, filed Jan. 24, 2005, De La Mettrie, et al.
U.S. Appl. No. 11/043,285, filed Jan. 27, 2005, Grollier, et al.
U.S. Appl. No. 11/040,002, filed Jan. 24, 2005, Grollier, et al.
U.S. Appl. No. 11/044,351, filed Jan. 28, 2005, De La Mettrie.
G. Metz, "Haufig, Vielfaltig, aber wenig beachtet", Pharmazeutische Zeitung, vol. 51, 2000, pp. 4400-4405, XP002294546.
G. Metz, Teetrinken als Konigsdisziplin, Pharmazeutische Zeitung, vol. 31, 2000, pp. 2526-2530, XP002294547.

* cited by examiner

*Primary Examiner*—Eisa B Elhilo
(74) *Attorney, Agent, or Firm*—Oblon, Spivak, McClelland, Maier & Neustadt, P.C.

(57) ABSTRACT

According to the invention the process for preparing a composition includes a step of percolating a fluid, preferably at a temperature greater than or equal to 30° C., more preferably ranging from 30 to 150° C., very preferably from 40° C. to 120° C., under a pressure of at least 3 bars (3×105 Pa) through at least one protective agent for keratin fibers, in solid or pasty form.

18 Claims, No Drawings

COMPOSITION FOR PROTECTING KERATIN MATERIAL, PROCESS OF MAKING, USES THEREOF

REFERENCE TO PRIOR APPLICATIONS

This application claims priority to U.S. provisional application 60/545,188 filed Feb. 18, 2004, and to French patent application 0400851 filed Jan. 29, 2004, both incorporated herein by reference.

FIELD OF THE INVENTION

The present invention relates to a composition obtained from pressurized fluid and at least one agent for protecting keratin fibers. It also relates to a process for preparing such compositions and to methods for treating keratin fibers.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

It is well known that keratin fibers such as the hair, eyelashes or eyebrows are sensitized or weakened to various degrees by the action of atmospheric agents and of light, development of greasiness, and chlorine, and also by the repeated action of various more or less aggressive treatments, such as permanent waves, straightening, dyeing, bleaching, washing and others. The hair then becomes rough to the touch and is difficult to disentangle and to style. Moreover, the mechanical properties of the keratin fibers, such as tensile strength, breaking load and elasticity, are adversely affected over time.

Compositions can then be applied to these keratin fibers, comprising agents which protect the keratin fibers, such as sunscreens or flavonoids.

As used herein, "agents which protect keratin fibers" mean agents which protect the keratin fibers against aggressive external influences, particularly those described above.

As used herein, "protection of keratin fibers against aggressive external influences" and "protection of keratin fibers" means the reduction in the adverse effect on the physico-chemical properties of the keratin fibers, and in particular the tensile strength, breaking load and elasticity, under the action of the external agents. This cosmetic effect is manifested in an improved appearance of the fibers.

However, the (cosmetic treatment) compositions comprising such protective agents are generally aqueous compositions in which the agents must be solubilized. The lack of solubility of these compounds lessens the treatment power of these compositions. Furthermore, this solubility criterion reduces the number of water-insoluble protective agents that can be used for the cosmetic treatment of keratin fibers. This is particularly the case with compounds having a high melting point.

DETAILED DESCRIPTION OF THE INVENTION

It has now been discovered, surprisingly, that by using a particular process for preparing a composition for, e.g., cosmetic treatment of keratin fibers, it is possible to obtain within a very short time, e.g., less than 2 minutes, compositions which have a greater or lesser concentration of protective agent(s), preferably without preservative, which allows the solubility problems set out above to be overcome.

This process is simple to implement. A pressurized fluid whose temperature is preferably greater than or equal to 30° C. and more preferably ranges from 30 to 150° C. is passed for a very short period of time, e.g., less than one minute, through at least one protective agent in solid or pasty form, preferably in solid form and more preferably in pulverulent form.

The process makes it possible to use, in anhydrous form, protective agents which are unstable in aqueous compositions, either because they react with water or because they react in aqueous solution with compounds which do not react with them in an anhydrous composition.

The compositions prepared according to this process may have a limited storage stability, which is not a disadvantage here, since the process leads to a ready-to-use composition which is intended to be used rapidly after its preparation, for example, within 5 minutes following its preparation, in particular after cooling to a cosmetically acceptable temperature, preferably less than 60° C. The composition may be used for up to one week or more after its preparation, depending on the rate of degradation of the protective agent used.

Given the very short preparation time, the (cosmetic treatment) compositions may be prepared "on demand" by mixing various cosmetically active compounds in accordance with the desired cosmetic properties.

According to another embodiment the protective agents may be packaged in a ready-to-use device, and it is not necessary to determine beforehand the concentrations of the agents in solution, thereby limiting measurement errors on the part of the user.

Furthermore, the process according to the invention allows the use of multi-compartment bottles to be avoided, thereby making the process particularly economical and more reliable for the user.

The composition obtained in this way may be used alone or in a mixture with another composition.

An additional advantage of this preparation process is that compositions are obtained which impart good cosmetic properties. In particular the keratin fibers treated with a composition obtained by the process according to the invention exhibit good properties of resistance to aggressive external influences, and particularly against pollution, development of greasiness, UV radiation, light, free radicals and chlorine.

The invention accordingly provides for the use of a composition obtained by percolating a fluid under a pressure of at least 3 bars through at least one protective agent for keratin fibers, in solid or pasty form, for protecting keratin fibers against aggressive external influences.

The invention also provides a process for preparing a composition for cosmetic treatment of keratin fibers which comprises a step of percolating a fluid under a pressure of at least 3 bars through at least one sunscreen in solid or pasty form.

The invention further provides a composition obtainable by the process according to the invention.

The invention also provides a packaging device which allows the preparation process of the present invention to be implemented.

Further subject matter, characteristics, aspects and advantages of the invention will emerge more clearly from a reading of the further description and examples which follow.

Preferably the keratin fibers are the hair.

The use of the composition obtained by percolating a fluid under a pressure of at least 3 bars through at least one protective agent for keratin fibers, in solid or pasty form, allows the keratin fibers to be protected against aggressive external influences, and particularly against pollution, development of greasiness, UV radiation, light, free radicals and chlorine, especially against UV radiation.

According to the invention the process for preparing a composition includes a step of percolating a fluid, preferably at a temperature greater than or equal to 30° C., more preferably ranging from 30 to 150° C., very preferably from 40° C. to 120° C., under a pressure of at least 3 bars (3×105 Pa) through at least one protective agent for keratin fibers, in solid or pasty form.

Percolation is a movement of fluid through a saturated porous medium which allows the passage of the fluid under the action or effect of pressure.

The fluid may be composed of water vapour, e.g., steam, optionally accompanied by liquid water, or of one or more cosmetically acceptable liquid and/or gaseous solvents, especially organic solvents, or else of a mixture of water vapour, optionally accompanied by liquid water, and one or more cosmetically acceptable liquid and/or gaseous solvents. Preferably the fluid comprises at least water vapour, which may be accompanied by liquid water, and more preferably it is water vapour which may be accompanied by liquid water.

Useful organic solvents include, for example, lower C1-C4 alcohols, such as ethanol and isopropanol; polyols and polyol ethers such as 2-butoxyethanol, propylene glycol, propylene glycol monomethyl ether, diethylene glycol monoethyl and monomethyl ether; and aromatic alcohols such as benzyl alcohol or phenoxyethanol, and mixtures thereof.

A "compound insoluble in water" is any compound which at a concentration greater than or equal to 0.1% by weight in water at 25° C. does not form a transparent isotropic solution to the naked eye.

The protective agent is in solid form or in pasty form, preferably in solid form, and more preferably in pulverulent form.

By "pasty form" in the sense of the present invention is meant a consistency intermediate between a solid phase and a liquid phase. The viscosity of this pasty phase is preferably greater than 0.1 Pa·s, and more preferably greater than 1 Pa·s, at 25° C. with a shear rate of 10 s-1.

The process of the present invention may be implemented on the basis of a conventional device allowing a fluid to be generated under pressure, at a temperature of preferably greater than or equal to 30° C., more preferably ranging from 30 to 150° C. A device of this kind comprises a pressure-resistant chamber, equipped with a heating block, and a circuit for conveying the fluid produced to the protective agent.

According to another embodiment the device comprises a reservoir for liquid(s) and also a pump allowing the liquid or liquids to be conveyed to the chamber.

The liquid contained in the reservoir is alternatively water or a cosmetically acceptable solvent or a mixture of two or more cosmetically acceptable solvents, or else a mixture of water and one or more cosmetically acceptable solvents. Preferably the liquid comprises at least water, and more preferably it is water.

One device particularly useful for the implementation of the process of the present invention is a coffee machine of the esspresso type. Machines of this kind are well known in the art. For example these machines are described in patents AT 168405, U.S. Pat. No. 2,688,911, DE 32433870 and IT 1265636.

According to one particular embodiment of the invention the percolation step is implemented with a fluid at a temperature greater than or equal to 30° C., and preferably ranging from 30 to 150° C., under a pressure of between 3 and 30 bars, or of at least 4 bars, preferably greater than 10 bars and very particularly between 10 and 30 bars.

According to one particular embodiment of the invention the percolation step is implemented with water vapour under a pressure of at least 4 bars, preferably greater than 10 bars and very particularly between 10 and 30 bars.

The protective agent or agents in solid or pasty form may be used directly in the device generating the pressurized fluid in a container intended for this purpose. They may also be packaged in a particular device for packaging a cosmetic composition, comprising a closed housing delimited by at least one wall which is at least partly permeable to a fluid under pressure of at least 3 bars, the composition comprising at least one protective agent for keratin fibers, in solid or pasty form. Devices of this kind are described for example in patent applications WO 00/56629, EP 512470 or WO 9903753.

According to one particular embodiment the housing is delimited by two sealed films. According to another embodiment the housing is delimited by a small dish closed by a lid.

These devices may be manufactured from woven or non-woven materials made of plastic or plant material, for example, made of cellulose, made of metal, such as aluminium, or made of composite material. Devices of this kind are described for example in patent applications WO 00/56629, EP 512470 or WO 9903753.

The protective agents which can be used in the process according to the invention may be selected from sunscreens, antioxidants, anti-pollution agents and free-radical scavengers. Use is made preferably of sunscreens. Mixtures can be used.

The sunscreens used in the invention are preferably selected from anthranilates; cinnamic derivatives; dibenzoylmethane derivatives; salicylic derivatives; camphor derivatives; triazine derivatives such as those described in patent applications U.S. Pat. No. 4,367,390, EP 863145, EP 517104, EP 570838, EP 796851, EP 775698, EP 878469, EP 933376, EP 507692, EP 507691, EP 790243 and EP 944624; benzophenone derivatives; β,β-diphenylacrylate derivatives; benzotriazole derivatives; benzalmalonate derivatives; benzimidazole derivatives; imidazolines; bisbenzoazolyl derivatives such as those described in patents EP 669323 and U.S. Pat. No. 2,463,264; p-aminobenzoic acid (PABA) derivatives; methylenebis(hydroxyphenylbenzotriazole) derivatives as described in applications U.S. Pat. No. 5,237,071, U.S. Pat. No. 5,166,355, GB 2303549, DE 19726184 and EP 893119; benzoxazole derivatives as described in patent applications EP 0832642, EP 1027883, EP 1300137 and DE 10162844; screening polymers and screening silicones such as those described in particular in application WO 93/04665; α-alkylstyrene-derived dimers such as those described in patent application DE 19855649; 4,4-diarylbutadienes such as those described in applications EP 0967200, DE 19746654, DE 19755649, EP-A-1008586, EP 1133980 and EP 1133981, and mixtures thereof.

As an example of organic screening agents mention may be made of those designated below under their INCI name:

Para-Aminobenzoic Acid Derivatives:
PABA,
Ethyl PABA,
Ethyl dihydroxypropyl PABA,
Glyceryl PABA;
Salicylic Derivatives:
Dipropylene glycol salicylate sold under the name Dipsal by Scher,
TEA salicylate, sold under the name Neo Heliopan TS by Haarmann & Reimer;
Dibenzoylmethane Derivatives:
Butylmethoxydibenzoylmethane, sold in particular under the trade name Parsol 1789 by Roche Vitamins,
Isopropyldibenzoylmethane,
Cinnamic Derivatives:
Ethylhexyl methoxycinnamate sold in particular under the trade name Parsol MCX by Roche Vitamins,
Isopropyl methoxycinnamate,
Isoamyl methoxycinnamate sold under the trade name Neo Heliopan E 1000 by Haarmann & Reimer,
DEA methoxycinnamate, diisopropyl methylcinnamate,
Glyceryl ethylhexanoate dimethoxycinnamate;
β,β-Diphenylacrylate Derivatives:
Ethocrylene, sold in particular under the trade name Uvinul N35 by BASF,
Benzophenone Derivatives:
Benzophenone-1 sold under the trade name Uvinul 400 by BASF,
Benzophenone-2 sold under the trade name Uvinul D50 by BASF,
Benzophenone-3 or oxybenzone sold under the trade name Uvinul M40 by BASF,
Benzophenone-4 sold under the trade name Uvinul MS40 by BASF,
Benzophenone-5,
Benzophenone-6 sold under the trade name Helisorb 11 by Norquay,
Benzophenone-8 sold under the trade name Spectra-Sorb TV-24 by American Cyanamid,
Benzophenone-9 sold under the trade name Uvinul DS-49 by BASF,
Benzophenone-12,
n-Hexyl 2-(4-diethylamino-2-hydroxybenzoyl)benzoate sold under the trade name Uvinul A Plus by BASF,
Benzylidenecamphor Derivatives:
3-Benzylidenecamphor manufactured under the name Mexoryl SD by Chimex,
4-Methylbenzylidenecamphor sold under the name Eusolex 6300 by Merck,
Benzylidenecamphorsulphonic acid manufactured under the name Mexoryl SO by Chimex,
Camphor benzalkonium methosulphate manufactured under the name Mexoryl SO by Chimex,
Terephthalylidenedicamphorsulphonic acid manufactured under the name Mexoryl SX by Chimex,
Polyacrylamidomethylbenzylidenecamphor manufactured under the name Mexoryl SW by Chimex,
Phenylbenzimidazole Derivatives:
Phenylbenzimidazolesulphonic acid sold in particular under the trade name Eusolex 232 by Merck,
Disodium phenyldibenzimidazoletetrasulphonate sold under the trade name Neo Heliopan AP by Haarmann & Reimer, Triazine Derivatives:
Anisotriazine sold under the trade name Tinosorb S by Ciba Geigy,
Ethylhexyltriazone sold in particular under the trade name Uvinul T150 by BASF,
Diethylhexylbutamidotriazone sold under the trade name Uvasorb HEB by Sigma 3V,
Phenylbenzotriazole Derivatives:
Drometrizole trisiloxane sold under the name Silatrizole by Rhodia Chimie
Methylenebisbenzotriazolyltetramethylbutylphenol, sold under the trade name Mixxim BB/100 by Fairmount Chemical or in micronized form in aqueous dispersion under the trade name<<Tinosorb M by Ciba Specialty Chemicals,
Anthranilic Derivatives:
Methyl anthranilate sold under the trade name Neo Heliopan MA by Haarmann & Reimer,
Imidazoline Derivatives;
Ethylhexyl dimethoxybenzylidenedioxoimidazolinepropionate,
Benzalmalonate Derivatives
Polyorganosiloxanes containing a benzalmalonate function, such as the Polysilicone-15 sold under the trade name Parsol SLX by Roche Vitamins;
4,4-Diarylbutadiene Derivatives:
1,1-Dicarboxy(2,2'-dimethylpropyl)-4,4-diphenylbutadiene;
Benzoxazole Derivatives:
2,4-Bis[5-1(dimethylpropyl)benzoxazol-2-yl-(4-phenyl)imino]-6-(2-ethylhexyl)imino-1,3,5-triazine sold under the name Uvasorb K2A by Sigma 3V;
and mixtures thereof.

The preferred organic UV screening agents are selected from:
Ethylhexyl Methoxycinnamate,
Butyl Methoxydibenzoylmethane,
Phenylbenzimidazole Sulphonic Acid,
Benzophenone-3,
Benzophenone-4,
Benzophenone-5,
n-Hexyl 2-(4-diethylamino-2-hydroxybenzoyl)benzoate,
4-Methylbenzylidene camphor,
Terephthalylidene Dicamphor Sulphonic Acid,
Disodium Phenyl Dibenzimidazole Tetra-sulphonate,
Anisotriazine,
Ethylhexyl triazone,
Diethylhexyl Butamido Triazone,
Methylene bis-Benzotriazolyl Tetramethylbutylphenol,
Drometrizole Trisiloxane,
Polysilicone-15,
1,1-Dicarboxy(2,2'-dimethylpropyl)-4,4-diphenylbutadiene,
2,4-bis[5-1(Dimethylpropyl)benzoxazol-2-yl(4-phenyl)imino]-6-(2-ethylhexyl)imino-1,3,5-triazine,
and mixtures thereof.

The term "anti-pollution agent" refers to any compound capable of trapping ozone, mono- or polycyclic aromatic compounds such as benzopyrene and/or heavy metals such as cobalt, mercury, cadmium and/or nickel. A "free-radical scavenger" is any compound capable of trapping free radicals.

As ozone-trapping agents which can be used in the composition according to the invention mention may be made in particular of vitamin C and its derivatives, including ascorbyl glucoside; non-colouring phenols and polyphenols, especially tannins, ellagic acid and tannic acid; epigallocatechin and natural extracts containing it; olive leaf extracts; tea extracts, in particular green tea extracts; anthocyanins; rosemary extracts; phenol acids, especially chlorogenic acid; stilbenes, especially resveratrol; sulphur-containing amino acid derivatives, especially S-carboxymethylcysteine; ergothioneine; N-acetylcysteine; chelating agents such as N,N'-bis(3,4,5-trimethoxybenzyl)ethylenediamine or one of its salts, metal complexes or esters; carotenoids such as crocetin; and various primary materials, such as the mixture of arginine, histidine ribonucleate, mannitol, adenosine triphosphate, pyridoxine, phenylalanine, tyrosine and hydrolysed RNA marketed by Laboratoires Sérobiologiques under the trade name CPP LS 2633-12F®, the water-soluble maize fraction marketed by the company Solabia under the trade name Phytovityl®, the mixture of extract of fumitory and extract of lemon marketed under the name Unicotrozon C-49® by the company Induchem, and the mixture of extracts of ginseng, apple, peach, wheat and barley sold by the company Provital under the trade name Pronalen Bioprotect®.

As agents which trap aromatic mono- or polycyclic compounds and can be used in the composition according to the invention mention may be made in particular of tannins such as ellagic acid; non-colouring indole derivatives, especially 3-indolecarbinol; tea extracts, especially green tea extracts, extracts of water hyacinth or *Eichhornia crassipes*; and the water-soluble maize fraction marketed by the company Solabia under the trade name Phytovityl®.

Finally, as agents which trap heavy metals and can be used in the composition according to the invention mention may be made in particular of chelating agents such as EDTA, the pentasodium salt of ethylenediaminetetramethylenephosphonic acid, and N,N'-bis(3,4,5-trimethoxybenzyl) ethylenediamine or one of its salts, metal complexes or esters; phytic acid; chitosan derivatives; tea extracts, especially green tea extracts; tannins such as ellagic acid; sulphur-containing amino acids such as cysteine; extracts of water hyacinth (*Eichhornia crassipes*); and the water-soluble maize fraction marketed by the company Solabia under the trade name Phytovityl®.

The free-radical scavengers or antioxidants which can be used in the composition according to the invention include, besides certain anti-pollution agents mentioned above, vitamin E and its derivatives such as tocopheryl acetate; flavonoids; bioflavonoids; coenzyme Q10 or ubiquinone; certain enzymes such as catalase, superoxide dismutase, lactoperoxidase, glutathione peroxidase and quinone reductases; glutathione; benzylidenecamphor; benzylcyclanones; substituted naphthalenones; pidolates; phytantriol; gamma-oryzanol; guanosine; lignans; melatonin, reductones and derivatives thereof, including erythorbic acid, ascorbic acid and ascorbyl palmitate, and sodium sulphite.

As flavonoids mention may be made, for example, of isoflavonoids, which constitute a sub-class of the flavonoids, formed by a 3-phenylchroman skeleton which may comprise various substituents and different levels of oxidation. The term "isoflavonoid" refers to a number of classes of compound, among which mention may be made of isoflavones, isoflavanones, rotenoids, pterocarpans, isoflavans, isoflavan-3-enes, 3-arylcoumarins, 3-aryl-4-hydroxycoumarins, coumestans, coumaronochromes, α-methyldeoxybenzoins, 2-arylbenzofurans, and mixtures thereof. In this context reference may be made advantageously, for a complete review of the isoflavonoids, the methods of analysing them, and their sources, to Chapter 5, "Isoflavonoids", written by P. M. Dewick, in The Flavonoids, edited by Harbone, pp. 125-157 (1988).

The isoflavonoids may be of natural or synthetic origin. By "natural origin" is meant isoflavonoid in the pure state or as a solution at various concentrations, obtained by various processes of extraction from an element, generally a plant, of natural origin. By "synthetic origin" is meant isoflavonoid in the pure state or in solution at various concentrations, obtained by chemical synthesis.

Among bioflavonoids mention may be made of citrus bioflavonoids. Citrus bioflavonoids are present in the peels of citrus fruits such as lemon, orange, mandarin or grapefruit. They are also known for their aptitude at keeping blood vessels in good condition, by reducing the fragility and permeability of capillary vessels (The Merck Index; 1989; page 1243).

The bioflavonoids which can be used in the context of the present invention may be selected from the compounds of formula (I):

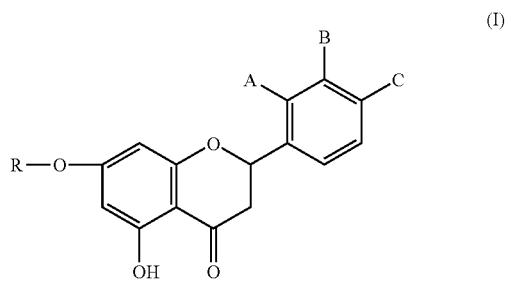

in which
R represents a radical of a sugar,
A represents a hydrogen atom or an alkoxy radical having approximately 1 to 4 carbon atoms,
B represents a hydrogen atom or a hydroxyl radical or alkoxy radical having approximately 1 to 4 carbon atoms,
C represents a hydrogen atom or a hydroxyl radical or alkoxy radical having approximately 1 to 4 carbon atoms,
or of formula (II):

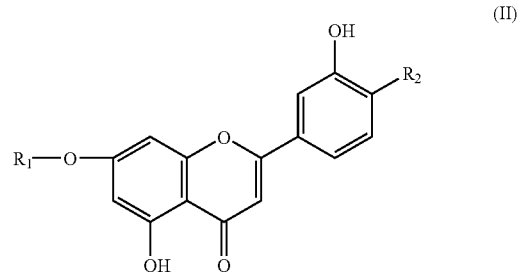

in which R1 denotes a 6-O-(6-deoxy-α-L-mannopyranosyl)-β-D-glucopyranosyl radical and R2 denotes an alkoxy radical having approximately 1 to 4 carbon atoms.

The bioflavonoids as defined by the formulae (I) or (II) above are treatment agents directed to the protection or enhancement of physical properties, especially mechanical properties and/or cosmetic properties of the keratinous epidermal derivatives (the hair, eyelashes, eyebrows and nails).

The mechanical properties enhanced are more particularly the tensile strength, breaking load or elasticity.

The cosmetic properties are, in particular, the disentangling and/or styling and/or softness.

In the context of the present invention A represents preferably a hydrogen atom or a methoxy radical, B and C represent, preferably and independently of one another, a hydrogen atom or a hydroxyl or methoxy radical, R2 represents preferably a methoxy radical. R represents preferably a residue selected from the moieties 6-O-(6-deoxy-α-L-mannopyranosyl)-β-D-glucopyranosyl, 2-O-(6-deoxy-α-L-mannopyranosyl)-β-D-glucopyranosyl and 6-deoxy-α-L-mannopyranosyl.

The compounds of formula (I) which are more particularly preferred are selected from naringine, neohesperidin, hesperidin and eriodictin.

The compounds of formula (I) and (II) are bioflavonoids which are extracted from plants and which may also be obtained in accordance with the processes described in "The Flavonoids", Harbone J. B., Mabry T. J., Helga Mabry, 1975.

The bioflavonoids which can be used according to the invention possess a high affinity for keratinous epidermal derivatives. They reinforce the physical properties of the keratinous epidermal derivatives, particularly against degradation by light. They preserve the mechanical properties of the keratinous epidermal derivatives, and particularly their tensile strength, their elasticity and their rate of swelling in an aqueous medium. The hair thus treated exhibits good cosmetic properties, particularly in terms of the ease with which it can be untangled.

The plants or plant extracts used may be subjected, prior to percolation, to a treatment such as roasting, cryogrinding or lyophilization, and combinations thereof.

The compounds of formula (I) and (II) are present in extracts of citrus fruits and in particular of lemon. Such extracts are marketed in particular by the company Interchemical under the names Citrus Bioflavonoid Complex 45%, Lemon Bioflavonoid Complex 50%, Grapefruit Bioflavonoid Complex 25% And Orange Bioflavonoid Complex 25%.

The protective agent or agents according to the invention may be employed in a mixture with one or solid or pasty, and preferably pulverulent, adjuvants. The adjuvants may be selected from clays, salts, anionic, cationic, nonionic, amphoteric and zwitterionic surfactants, natural or synthetic thickeners, glass beads, silica, nylon, alumina, titanium dioxide, zeolites, polymethyl methacrylate (PMMA), chitosan, maltodextrin, cyclodextrin, mono- or disaccharides such as glucose, sucrose, sorbitol or fructose, zinc oxide, zirconium oxide, resin particles such as silicone or silica beads, talc, polyaspartic acid, borosilicates, especially calcium borosilicate, polyethylene, cotton, polytetrafluoroethylene (PTFE), cellulose and its derivatives, superabsorbent compounds, magnesium carbonate or calcium carbonate, starch which optionally has been modified, maize seeds, polydimethylsiloxane gums, polyacrylamide, porous hydroxyapatite, silk, collagen, sawdust, fucus powder, flours or extracts of wheat, rice, pea, lupin, soya or barley, crosslinked polyvinylpyrrolidone, calcium alginate, activated carbon, poly(vinylidene chloride/acrylonitrile) particles, especially those marketed under the general name Expancel® by the company AKZO Nobel under the specific references Expancel®WE or DE Expancels, and mixtures thereof. Starting from the preparation process of the invention a (cosmetic treatment) composition is obtained which can be employed either directly or following addition of various components.

When one or more adjuvants are present the protective agent or agents of the invention is or are present preferably in an amount ranging from 0.5% to 99% by weight, more preferably from 1% to 80% by weight and even more preferably from 2% to 60% by weight relative to the total weight of protective agent(s) and adjuvants.

The composition for cosmetic treatment of keratin materials that is obtained according to the process of the invention comprises, in addition to the protective agent or agents and the compound(s) of the fluid, namely water and/or the cosmetically acceptable solvent(s), optionally all or part of the adjuvant or adjuvants present in the solid or pasty mixture.

Starting from the preparation process of the invention a composition for cosmetic treatment of keratin fibers is obtained which can be applied directly to the keratin fibers or which can be mixed with a cosmetically acceptable medium, or else at least one additive conventionally used in cosmetology can be added thereto by an operator. It is also possible to mix at least two compositions obtained by the process of the invention. The composition for cosmetic treatment of keratin fibers that results, where appropriate, from mixture(s) and/or addition(s) indicated above will be referred to hereinbelow as final (cosmetic treatment) composition or final composition.

One particular embodiment of the invention is applying the resulting composition using a device which does not require human intervention and which is optionally equipped with a cooling means.

The amount of the protective agent or agents present in the final (cosmetic treatment) composition obtained by the process of the present invention is generally preferably between 0.001% and 50% by weight approximately of the total weight of the final (cosmetic treatment) composition, more preferably between 0.005% and 30% and even more preferably between 0.01% and 20%.

When the (cosmetic) composition obtained by the process of the present invention is mixed with a cosmetically acceptable medium the medium is generally composed of water or of a mixture of water and at least one organic solvent in order to solubilize the compounds which would not be sufficiently soluble in the water.

As organic solvent mention may be made, for example, of lower C1-C4 alcohols, such as ethanol and isopropanol; polyols and polyol ethers such as 2-butoxyethanol, propylene glycol, propylene glycol monomethyl ether, diethylene glycol monoethyl and monomethyl ether; and aromatic alcohols, such as benzyl alcohol or phenoxyethanol, and mixtures thereof.

The solvents are preferably present in proportions of preferably between 1% and 40% by weight relative to the total weight of the final composition, and more preferably between 5% and 30% by weight.

At least one additive, for example those conventionally used in cosmetology, may also be added to the (cosmetic treatment) compositions obtained according to the process of the present invention. As examples of such additives mention may be made of anionic, cationic, nonionic, amphoteric and zwitterionic surfactants or mixtures thereof, anionic, cationic, nonionic, amphoteric and zwitterionic polymers or mixtures thereof, organic or inorganic thickeners, and especially anionic, cationic, nonionic and amphoteric polymeric associative thickeners, antioxidants, penetrants, sequestrants, perfumes, buffers, dispersants, conditioning agents such as, for example, silicone oils, film formers, ceramides, preservatives, opacifiers, and also oils, waxes, gums and coloured or nacreous pigments.

The above additives are generally present in an amount, respectively for each of them, of between 0.01% and 20% by weight relative to the weight of the final composition.

The person skilled in the art will of course take care that this or these optional compounds are selected such that the advantageous properties intrinsically attached to the cosmetic composition in accordance with the invention are not, or not substantially, adversely effected by the intended addition or additions.

The pH of the final composition is generally preferably between 3 and 12 and preferably between 5 and 11. It may be adjusted to the desired value by means of acidifying or alkalifying agents which are commonly used in cosmetology, or else with the aid of conventional buffer systems.

Among the acidifying agents mention may be made by way of example of organic or inorganic acids such as hydrochloric acid, orthophosphoric acid, sulphuric acid, carboxylic acids such as acetic acid, tartaric acid, citric acid and lactic acid, and sulphonic acids.

Among the alkalifying salts mention may be made, by way of example, of ammonia, alkali metal carbonates, alkanolamines such as mono-, di- and triethanolamines and derivatives thereof, sodium hydroxide or potassium hydroxide and the compounds of formula (II) below:

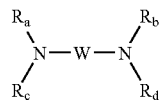

(II)

in which W is a propylene residue optionally substituted by a hydroxyl group or a C1-C4 alkyl radical; and Ra, Rb, Rc and Rd, which are identical or different, represent a hydrogen atom or a C1-C4 alkyl or C1-C4 hydroxyalkyl radical.

The final (cosmetic treatment) composition may be present in a variety of forms, such as in the form of liquids, creams or gels or any other form appropriate for realizing treatment of keratin materials, and especially keratin fibers, and of the skin.

The final (cosmetic treatment) composition may be used, for example, as a shampoo, conditioner, rinsed or non-rinsed care product, deep-down care mask, shower gel, lotion or cream for treating keratin fibers.

The invention likewise provides a process for preparing a cosmetic composition for the cosmetic treatment of keratin fibers, wherein it comprises a step of percolating a fluid under a pressure of at least 3 bars through at least one sunscreen in solid or pasty form.

It likewise provides the compositions obtained by this process, and also provides for their use for protecting keratin fibers against aggressive external influences. The compositions are preferably devoid of preservatives.

The invention further provides for the cosmetic use of a composition obtained by the process according to the invention for manufacturing a composition intended for protecting keratin fibers, and especially the skin, against aggressive external influences.

The compositions used in the present invention may be applied to the keratin fibers by means of an operator or by means of a device which does not require human intervention. The time of application may vary for example between 15 seconds and 1 hour.

Following (and/or prior to) application, the (cosmetic treatment) composition obtained according to the process of the invention may be mixed with a cosmetically acceptable medium and/or with one or more additives conventionally used in cosmetology, as described above.

Another embodiment is preparing at least two (cosmetic treatment) compositions according to the process of the invention, in mixing them and in adding, optionally, a cosmetically acceptable medium and/or one or more additives which are conventionally used in cosmetology, as described above, then in applying the resulting final composition to the keratin materials.

The use of sunscreens makes it possible to combat, in particular, UV radiation.

The examples below are intended to illustrate the present invention, but not limit it.

EXAMPLE 1

The following ingredients are mixed in the proportions indicated in % by weight relative to the total weight of solid mixture:

| | |
|---|---|
| cetyl stearyl alcohol/ethoxylated (30 EO) cetyl stearyl alcohol mixture sold under the trade name Sinnowax AO by the company Cognis | 40% |
| 2-phenylbenzimidazole-5-sulphonic acid sold under the trade name Eusolex 232 by the company Merck | 20% |
| sodium chloride | 40% |

5 g of this mixture are placed in an expresso machine. Water vapour is subsequently passed through until a composition (A) having a final volume of 50 ml is obtained.

Subsequently it is possible to add, to two parts by weight of composition (A), one part by weight of an aqueous composition (B) containing 1% by weight of hydroxyethylcellulose, in order to make application easier.

This gives a (cosmetic treatment) composition which is ready to be applied to the hair.

The resultant hair is resistant to aggressive external influences.

EXAMPLE 2

The following ingredients are mixed in the proportions indicated in % by weight relative to the total weight of solid mixture:

| | |
|---|---|
| cetyl stearyl alcohol/ethoxylated (30 EO) cetyl stearyl alcohol mixture sold under the trade name Sinnowax AO by the company Cognis | 40% |
| 2-hydroxy-4-methoxybenzophenonone-5-sulphonic acid sold under the trade name Uvinul MS 40 by the company BASF | 20% |
| chicory-root inulin sold under the trade name Frutafit IQ by the company Cosun | 40% |

5 g of this mixture are placed in an expresso machine. Water vapour is subsequently passed through until a composition (A) having a final volume of 50 ml is obtained.

Subsequently it is possible to add, to two parts by weight of composition (A), one part by weight of an aqueous composition (B) containing 1% by weight of hydroxyethylcellulose, in order to make application easier.

This gives a (cosmetic treatment) composition which is ready to be applied to the hair.

The resultant hair is resistant to aggressive etrenal influences.

The above written description of the invention provides a manner and process of making and using it such that any person skilled in this art is enabled to make and use the same, this enablement being provided in particular for the subject matter of the appended claims, which make up a part of the original description and including a process for preparing a (cosmetic) composition useful for treating keratin materials, wherein it comprises a step of percolating a fluid under a pressure of at least 3 bars through at least one protective agent for keratin fibers, in solid or pasty form, the compositon prepared, and a process using the composition for protecting keratin fibers against aggressive external influences.

As used herein, the phrases "selected from the group consisting of," "chosen from," "selected from," and the like include mixtures of the specified materials.

Where compounds are described as, e.g., "vitamin C and its derivatives" an alternate is "vitamin C and vitamin C compounds" where vitamin C derivatives and compounds share a common core/structure with vitamin C. One of ordinary skill in the art knows how to identify derivatives and compounds of compound X based on the structure of X and the similarity in structure of the derivatives and compounds.

Where a term is enclosed by parentheses it is an optional modifier. For example, the term "(cosmetic treatment) composition" describes both a composition in general and a cosmetic treatment composition.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A process for preparing a composition, comprising percolating a fluid, at a pressure of at least 3 bar, through at least one protective agent for keratin fibers, in solid or pasty form, wherein the at least one protective agent is selected from sunscreens, antioxidants, anti-pollution agents, free-radical scavengers, and mixtures thereof.

2. The process according to claim 1, comprising percolating a fluid, at a pressure of at least 3 bar, through at least one sunscreen.

3. The process according to claim 2, wherein the at least one sunscreen is selected from anthranilates, cinnamic derivatives, dibenzoylmethane derivatives, salicylic derivatives, camphor derivatives, triazine derivatives, benzophenone derivatives, β, β-diphenylacrylate derivatives, benzotriazole derivatives, benzalmalonate derivatives, benzimidazole derivatives, imidazolines, bisbenzoazolyl derivatives, p-aminobenzoic acid derivatives, methylenebis(hydroxyphenylbenzotriazole) derivatives, benzoxazole derivatives, screening polymers and screening silicones, α-alkylstyrene-derived dimers, 4,4-diarylbutadienes, and mixtures thereof.

4. The process according to claim 1, comprising percolating a fluid, at a pressure of at least 3 bar, through at least one anti-pollution agent, wherein the at least one anti-pollution agent is selected from vitamin C and its derivatives, non-colouring phenols and polyphenols, epigallocatechin and natural extracts containing it, olive leaf extracts, tea extracts, anthocyanins, rosemary extracts, phenol acids, stilbenes, sulphur-containing amino acid derivatives, N-acetylcysteine, chelating agents, carotenoids, non-colouring indole derivatives, and mixtures thereof.

5. The process according to claim 1, comprising percolating a fluid, at a pressure of at least 3 bar, through at least one free-radical scavenger and/or antioxidant selected from vitamin E and its derivatives, flavonoids, bioflavonoids, coenzyme Q10 or ubiquinone, catalase, superoxide dismutase, lactoperoxidase, glutathione peroxidase and quinone reductases, glutathione, benzylidenecamphor, benzylcyclanones, substituted naplithalenones, pidolates; phytantriol, gamma-oryzanol, guanosine, lignans, melatonin, reductones and the derivatives thereof, including erythorbic acid, ascorbic acid and ascorbyl palmitate, sodium suiphite, and mixtures thereof.

6. The process according to claim 1, wherein the protective agent in solid or pasty form is present as a mixture with at least one adjuvant.

7. The process according to claim 6, wherein the adjuvant is selected from clays, salts, anionic, nonionic, cationic or zwitterionic surfactants, natural or synthetic thickeners, starch which optionally has been modified, glass beads, silica, nylon, alumina, titanium dioxide, zeolites, poly(methyl methacrylate) (PMMA), chitosan, maltodextrin, cyclodextrin, mono- or disaccharides, zinc oxide, zirconium oxide, resin particles such as silicone or silica beads, talc, polyaspartic acid, borosilicates, especially calcium borosilicate, polyethylene, cotton, polytetrafluoroethylene (PTFE), cellulose and its derivatives, superabsorbent compounds, magnesium carbonate or calcium carbonate, maize seeds, polydimethylsiloxane gums, polyacrylamide, porous hydroxyapatite, silk, collagen, sawdust, fucus powder, flours or extracts of wheat, rice, pea, lupin, soya or barley, crosslinked polyvinylpyrrolidone, calcium alginate, activated carbon, poly(vinylidene chloride/acrylonitrile) particles, and mixtures thereof.

8. The process according to claim 6, wherein the protective agent or agents are present in an amount ranging from 0.5% to 99% by weight relative to the total weight of protective agent(s) and adjuvant.

9. The process according to claim 1, wherein the percolation step is performed with a fluid under a pressure of 3-30 bars.

10. The process according to claim 1, wherein the fluid comprises steam.

11. The process according to claim 10, wherein the fluid is steam accompanied by liquid water.

12. The process according to claim 1, wherein the fluid comprises one or more cosmetically acceptable gaseous and/or liquid organic solvents.

13. The process according to claim 1, wherein said composition is devoid of preservative.

14. A process, comprising preparing a composition comprising percolating a fluid, at a pressure of at least 3 bar, through at least one protective agent for keratin fibers, in solid or pasty form, and to apply said composition to keratin material.

15. The process according to claim 14, wherein the composition is applied to keratin fiber by a device which does not require human intervention.

16. A process according to claim 14, wherein, before application, the composition is mixed with a cosmetically acceptable medium and/or with one or more additives used in cosmetics, and or with another composition prepared by a process comprising percolating a fluid, at a pressure of at least 3 bar, through at least one protective agent for keratin fibers, in solid or pasty form.

17. A process according to claim 14, wherein the composition is applied in an amount effective to resist pollution, development of greasiness, UV radiation, light, free radicals and/or chlorine.

18. A device for packaging a composition, comprising a closed housing delimited by at least one wall that is at least partially permeable to fluid at a pressure of at least 3 bar, the device having therein a composition comprising at least one protective agent for keratin fibers, in solid or pasty form, the device being optionally delimited by two sealed sheets or by a tray closed with a lid, wherein the at least one protective agent is selected from sunscreens, antioxidants, anti-pollution agents, free-radical scavengers, and mixtures thereof.

* * * * *